US009360308B2

(12) United States Patent
Hwang et al.

(10) Patent No.: US 9,360,308 B2
(45) Date of Patent: Jun. 7, 2016

(54) METHODS FOR MEASURING A THICKNESS OF AN OBJECT

(71) Applicant: SAMSUNG ELECTRONICS CO., LTD., Suwon-si, Gyeonggi-do (KR)

(72) Inventors: Byung Hyun Hwang, Yongin-si (KR); Kwang-Hoon Kim, Yongin-si (KR); Woongkyu Son, Hwaseong-si (KR); Chulgi Song, Yongin-si (KR); Choonshik Leem, Seoul (KR)

(73) Assignee: SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 106 days.

(21) Appl. No.: 14/248,673

(22) Filed: Apr. 9, 2014

(65) Prior Publication Data

US 2015/0010133 A1  Jan. 8, 2015

(30) Foreign Application Priority Data

Jul. 3, 2013 (KR) .................. 10-2013-0077780

(51) Int. Cl.
*G01N 23/20* (2006.01)
*G01B 15/02* (2006.01)

(52) U.S. Cl.
CPC ............. *G01B 15/02* (2013.01); *G01N 23/20* (2013.01)

(58) Field of Classification Search
CPC ... G01N 23/20; G01N 23/203; G01N 23/207; G01B 15/00; G01B 15/02; G21K 1/06

USPC ..................................... 378/70, 89
See application file for complete search history.

(56) References Cited

U.S. PATENT DOCUMENTS

| 6,643,354 | B2 * | 11/2003 | Koppel | G01N 23/20 378/86 |
| 6,668,038 | B2 | 12/2003 | Kataoka et al. | |
| 6,754,305 | B1 * | 6/2004 | Rosencwaig | G01B 15/02 257/E21.53 |
| 7,046,760 | B2 | 5/2006 | Kim et al. | |
| 7,302,034 | B2 | 11/2007 | Grodzins | |
| 2012/0294420 | A1 | 11/2012 | Nagai | |

FOREIGN PATENT DOCUMENTS

| JP | 2001-318063 | 11/2001 |
| JP | 2003-318117 | 11/2003 |
| JP | 2008-175766 | 7/2008 |
| JP | 2011-163937 | 8/2011 |
| KR | 10-2006-0076063 A | 7/2006 |
| KR | 10-2008-0039055 A | 5/2008 |
| KR | 10-2009-0074604 A | 7/2009 |
| KR | 10-2010-0009038 A | 1/2010 |
| KR | 10-2010-00040439 A | 4/2010 |

* cited by examiner

*Primary Examiner* — Jurie Yun
(74) *Attorney, Agent, or Firm* — Lee & Morse, P.C.

(57) ABSTRACT

A method for analyzing an object includes measuring a first reflectivity of light from a surface and measuring a second reflectivity of light from the object, after the object is formed on the surface. A variation between the first and second reflectivities is calculated, and the variation is transformed by a predetermined transform. A thickness of the object is determined based on the transformed variation.

17 Claims, 4 Drawing Sheets

METHODS FOR MEASURING A THICKNESS OF AN OBJECT

CROSS-REFERENCE TO RELATED APPLICATION

Korean Patent Application No. 10-2013-0077780 filed on Jul. 3, 2013, and entitled, "METHODS FOR MEASURING A THICKNESS OF AN OBJECT," is incorporated by reference herein in its entirety.

BACKGROUND

1. Field

One or more embodiments described herein relate to a semiconductor device.

2. Description of the Related Art

Various processes are used to manufacture a semiconductor device. These processes include a deposition process, an ion implantation process, a photolithography process, a cleaning process, and a polishing process. These processes may be repeatedly performed to form a plurality of semiconductor devices on a wafer.

More accurate thickness measurements are required as the patterns in a semiconductor device become finer. One approach for measuring thickness involves radiating light and/or a sound waves to a specimen and detecting changes in the light and/or a sound waves. However, errors may occur in specific cases using this approach.

Another method known as spectroscopic ellipsometry (SE) uses an ultraviolet (UV) rays. In this method, thickness is measured based on changes in the phase of polarized light on a measurement target layer of a specimen. The SE method has a high resolution capable of measuring thickness in the range of several angstroms (Å).

In implementing the SE method, an optical constant value of the measurement target layer may be expressed as a mathematical function. A change in polarized light by the measurement target layer is then divided into components such as a thickness, a dispersive term, and an absorptive term.

However, the SE method has drawbacks. For example, some materials to be measured are difficult to express by a specific function. Additionally, light change conditions of thin layers of a multi-layer having a complex structure may be similar to each other. Thus, correlation between the thin layers may be high. As a result, it may be difficult to measure accurate thickness of a multi-layer having the complex structure using the SE method.

Furthermore, in manufacturing processes of semiconductor devices, a composite layer may be complex, a new material may be applied to a single layer, and/or physical properties of thin layers may be greatly changed by new processes. Thus, it may be difficult to accurately measure thickness of a thin layer.

SUMMARY

In accordance with one embodiment, a method for analyzing an object includes measuring a first X-ray reflectivity from a substrate before formation of the object; forming the object on the substrate; measuring a second X-ray reflectivity from the substrate after the formation of the object; calculating a variation between the first and second X-ray reflectivities; transforming the calculated variation using a fast-Fourier transform; and determining a thickness of the object based on the transformed calculated variation.

The method may include irradiating an X-ray for measuring each of the first and second X-ray reflectivities at an angle of about 5 degrees or less with respect to a surface of the substrate.

Measuring the first X-ray reflectivity may include measuring a first X-ray reflectivity spectrum, and measuring the second X-ray reflectivity may include measuring a second X-ray reflectivity spectrum. The method may further include generating a delta-spectrum between the first and second X-ray reflectivity spectrums. Calculating the variation may include subtracting a raw first X-ray reflectivity spectrum from a raw second X-ray reflectivity spectrum. The object is may be a layer or a pattern. The layer or pattern may be included in a semiconductor device.

The method may further include numerically expressing a full width at half maximum (FWMH) of a peak of a result obtained by fast-Fourier transforming the calculated variation, and/or numerically expressing a signal to noise ratio (S/N ratio) of a result obtained by fast-Fourier transforming the calculated variation.

In accordance with another embodiment, a method for analyzing an object includes measuring a first reflectivity of light from a surface; measuring a second reflectivity of light from the object, after the object is formed on the surface; calculating a variation between the first and second reflectivities; transforming the variation using a predetermined transform; and determining a thickness of the object based on the transformed variation. The light may be in an X-ray spectrum, and the predetermined transform may be a fast-Fourier transform.

The method may further include irradiating light on the surface at a first angle; and irradiating light on the object at a second angle. The first angle may be substantially equal to the second angle. The first and second angles may be in a range of about 5 degrees or less.

Measuring the first reflectivity may include measuring a first reflectivity spectrum, and measuring the second reflectivity may include measuring a second reflectivity spectrum. Calculating the variation may include subtracting a raw first reflectivity spectrum from a raw second reflectivity spectrum. The surface may be a surface of a semiconductor substrate, and the object may be a formation on the surface of the semiconductor substrate.

The method may include numerically expressing a full width at half maximum (FWMH) of a peak of a result obtained by the predetermined transform, and/or numerically expressing a signal to noise ratio (S/N ratio) of a result obtained by the predetermined transform.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1:
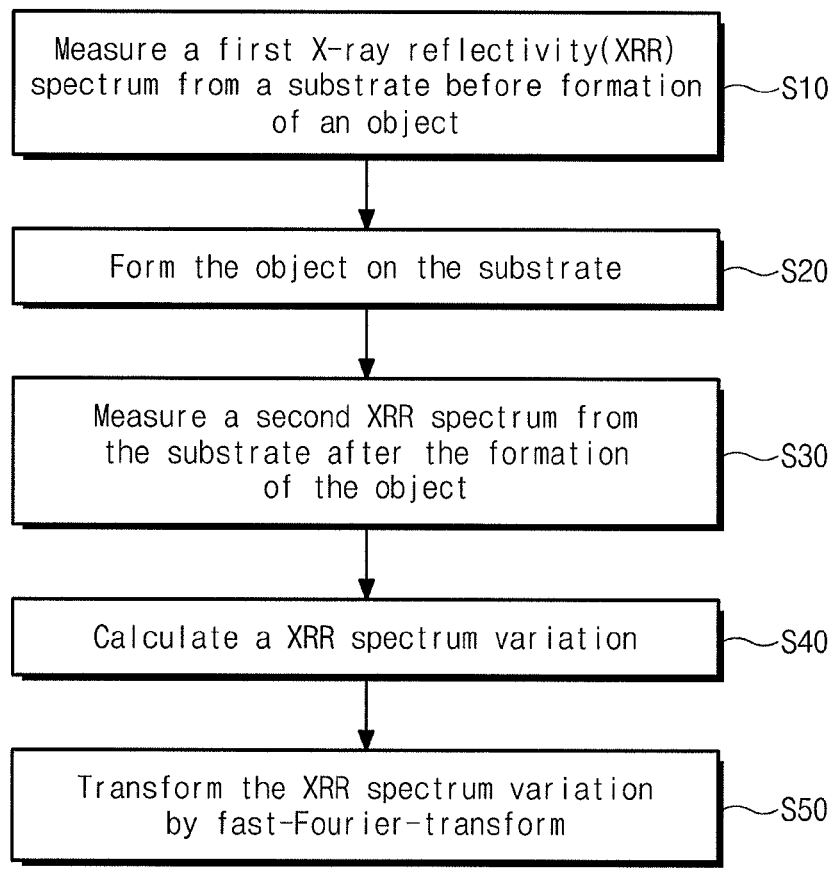
FIG. 1 illustrates one embodiment of a method for measuring thickness.

Example embodiments are described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

Overview

A complex refractive index may be expressed by Equation 1.

$$\tilde{n} = 1 - \delta + i\beta \quad (1)$$

In equation 1, ñ denotes the complex refractive index, δ denotes a dispersive term, and β denotes a absorptive term.

The dispersive term δ may be expressed by Equation 2.

$$\delta = \frac{r_0 \lambda^2}{2\pi} \cdot n_e = \frac{r_0 \lambda^2}{2\pi}(NZ/A)p_m \quad (2)$$

In equation 2, $r_0$ denotes an electron radius, λ denotes a wavelength of an X-ray, $n_e$ denotes an electron density, N denotes Avogadro's number, Z denotes an atomic number of an object, A denotes an atomic weight of the object, and $P_m$ denotes a material density of the object.

The absorptive term β may be expressed by Equation 3.

$$\beta = \frac{\lambda}{4\pi}\mu \quad (3)$$

In equation 3, λ denotes a wavelength of an X-ray and μ is an absorption coefficient.

A dispersive degree and absorptive degree in an X-ray wavelength band may be substantially 1 from the above equations. This is because a wavelength of Cu (Kα1), which is generally used as the wavelength of the wavelength of the X-ray in an X-ray reflectometry, is about 1.54 Å. For example, if the object irradiated with the X-ray is silicon (Si), all of the dispersive term ($\delta$=7.47×10$^{-6}$) and the absorptive term ($\beta$=0.18×10$^{-6}$) may be at a level of 10$^{-6}$ to 10$^{-7}$, so that the complex refractive index is close to about 1. In the case where the object is a silicon oxynitride (SiON) layer, the transmissivity of the X-rays is about 99.97% when X-rays having a wavelength of about 1.54 Å are irradiated to the object.

In the case where the X-ray wavelength band is used, the thickness of a thin layer may be measured so that influences by the dispersive term and absorptive term of the thin layer are substantially reduced or minimized.

Example Embodiments

Figure 2:
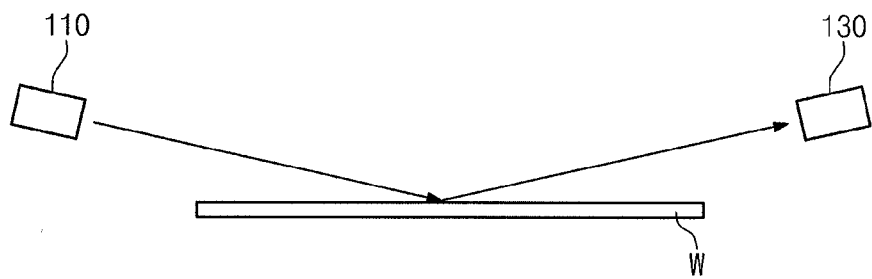
FIGS. 2 and 3 are diagrams illustrating operations included in the method for measuring thickness.
Figure 3:
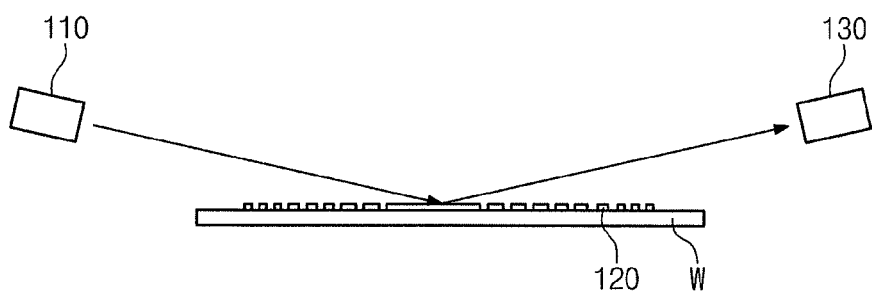

FIG. 1 illustrates an embodiment of a method for measuring the thickness of an object. FIGS. 2 and 3 illustrate different operations of this method. Referring to FIGS. 1 to 3, an X-ray emitted from an X-ray irradiator 110 is irradiated on a substrate W before formation of an object 120. Then, an X-ray reflected from the substrate W is detected by a detector 130 to measure a first X-ray reflectivity (XRR) (S10). The first measured X-ray reflectivity may be a spectrum of the X-ray reflected by the substrate W.

In one embodiment, the X-ray may be irradiated at an angle of about 5 degrees or less with respect to a surface of the substrate W. In other embodiments, the X-ray may be irradiated at a different angle, e.g., nearly parallel to the surface of the substrate W. If the X-ray is irradiated at an angle of about 0 degree to about 5 degrees with respect to the surface of the substrate W, interference fringes of variously reflected X-rays may be generated by a thickness, a density, and a surface of a thin layer, and/or a roughness of an interface between thin layers. The interference fringes may be analyzed to measure information such as the thickness, density, and roughness of the thin layer. This measurement method may be referred to as an X-ray reflectometry method.

A fitting simulation may be used to separate the thickness, density, and roughness information when reflection interference fringes of the X-ray reflectometry method are analyzed. At this time, it is possible for errors to occur. In order to reduce errors, the fitting simulation may be replaced by a fast-Fourier-transform (FFT). The FFT may be performed for repeated interferences fringes based on only the thickness information, for a fast-Fourier-transform (FFT) frequency of the repeated interference fringes. If the FFT frequency of the repeated interference fringes is converted into the thickness, the thickness information can be obtained through smaller suppositions and calculations.

In a next operation, object 120 is formed on substrate W (S20). The object 120 may be a thin layer or a pattern.

The X-ray emitted from the X-ray irradiator 110 is irradiated to the object 120 formed on the substrate W. Then, an X-ray reflected from the object 120 is detected by the detector 130 to measure a second X-ray reflectivity (S30). The measured second X-ray reflectivity may be a spectrum of the X-ray reflected by the object 120. An irradiation angle of the X-ray for measurement of the second X-ray reflectivity may be the same as that of the X-ray for the measurement of the first X-ray reflectivity.

The measuring method may further include generating a delta-spectrum between the first and second X-ray reflectivity spectrums.

A variation between the first and second X-ray reflectivities detected from the detector 130 is calculated (S40). The variation may be calculated by subtracting a raw first X-ray reflectivity spectrum from a raw second X-ray reflectivity spectrum. In other words, calculating the variation may include calculating a varied portion between a graph of the second X-ray reflectivity spectrum and a graph of the first X-ray reflectivity spectrum.

The calculated variation between the first and second X-ray reflectivities is transformed using the fast-Fourier-transform (S50). In one embodiment, the fast-Fourier-transform may be a feed-forward fast-Fourier-transform. In other words, the thickness of object 120 may be measured using an X-ray reflectometry spectrum feed-forward fast-Fourier-transform (XRR-SFP). Thus, the method for measuring the thickness of object 120 may further include converting the result obtained by the fast-Fourier-transform into information indicative of the thickness of the object 120.

If the object 120 is a single layer, the fast-Fourier-transform (FFT) frequency of the interference fringes may be directly converted into the thickness information of the object 120. However, if the object 120 is a multi-layer, interference fringes may be generated by a plurality of thin layers included in the multi-layer. Thus, if a lower thin layer disposed under the object 120 has a thickness similar to object 120 and is a different material from the object, fast-Fourier transform peaks similar to each other may be generated.

As a result, it may be difficult to measure the thickness of the object 120. In particular, if the lower thin layer having a similar thickness to the object 120 is a measurement target and has a reflection-intensity greater than the object 120 (in the X-ray reflectometry using a reflection interference fringe between thin layers), a thickness of the lower thin layer may be mistaken for the thickness of the object 120.

In this case, the X-ray reflectometry spectrum feed-forward fast-Fourier-transform (SRR-SFP) may be used in order to prevent the mistake described above. In one embodiment, the X-ray reflectometry spectrum feed-forward fast-Fourier-transform (SRR-SFP) may perform the fast-Fourier-transform on only a difference between intensities of reflected light. This may be performed according to the angle between the X-ray reflectivity spectrums before and after formation of the object 120. In other words, if the object 120 is a multi-layer, the interference fringes themselves are not directly fast-Fourier transformed.

The method for measuring the thickness of the object 120 may further include expressing a full width at half maximum (FWMH) of the peak of the result of the fast-Fourier transform numerically. Additionally, the method may include expressing a signal-to-noise ratio (S/N ratio) of the result of the fast-Fourier transform numerically. The numerical expressions of the result of the fast-Fourier transform may be used as references for judgment of reliability of the thickness of the measured object 120.

Figure 4:
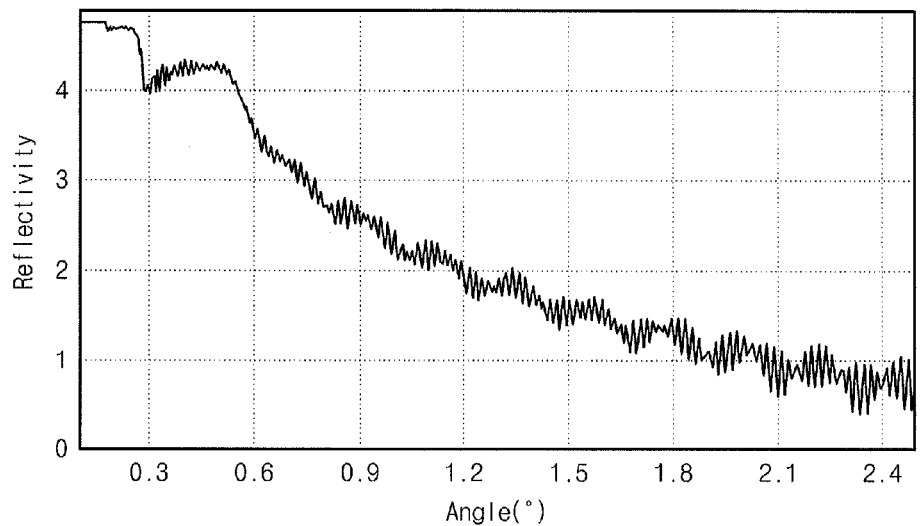
FIGS. 4 to 7 illustrate example results of the method.
Figure 5:
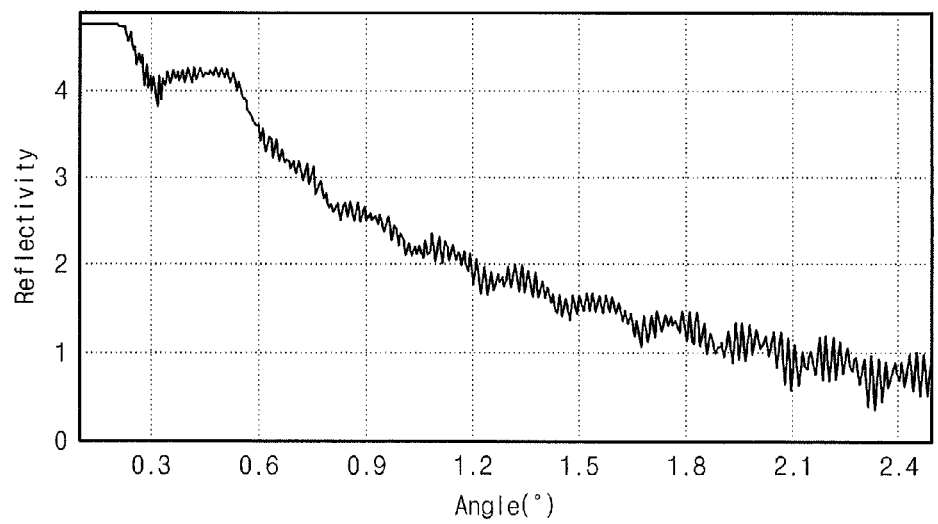
Figure 6:
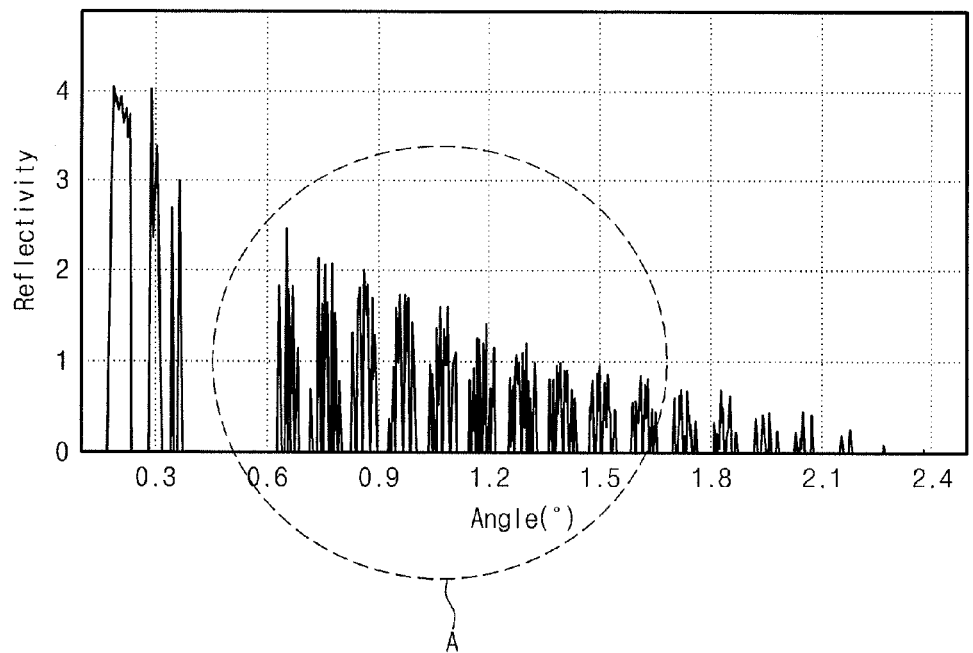
Figure 7:
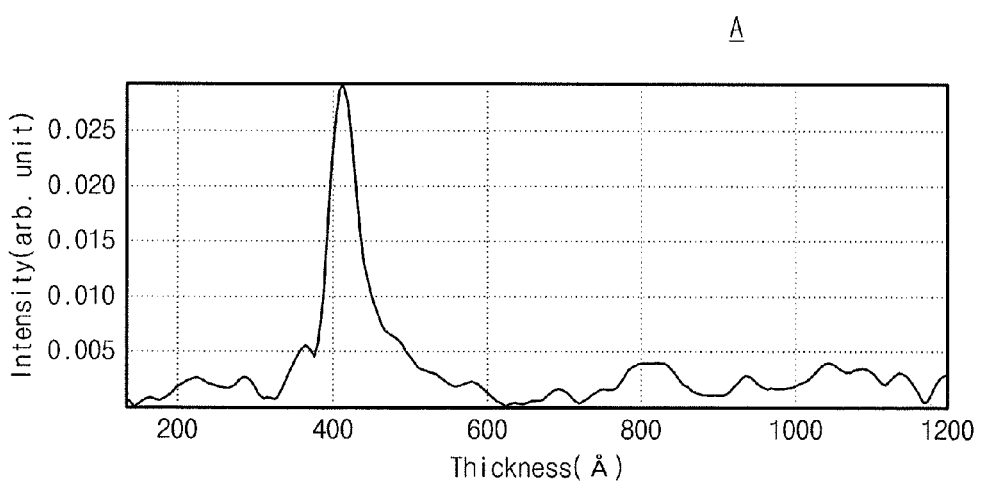

FIGS. 4 to 7 are graphs illustrating examples of results of the thickness-measuring method. FIG. 4 illustrates the first X-ray reflectivity spectrum of the substrate before the object is formed. FIG. 5 illustrates the second X-ray reflectivity spectrum of the substrate after the object is formed. FIG. 6 illustrates the variation between the first and second reflectivity spectrums. FIG. 7 illustrates the fast-Fourier transform result of portion A of FIG. 6.

Referring to FIG. 4, the first X-ray reflectivity spectrum is measured from the substrate (e.g., a silicon wafer) having a multi-layer including silicon oxide ($SiO_2$), tungsten (W), silicon nitride (SiN), silicon oxide, silicon, silicon nitride, and carbon (C) before the formation of the object. (See W of FIG. 2). The measured first X-ray reflectivity spectrum is illustrated in FIG. 4. In the graph of FIG. 4, the X-axis represents an irradiating angle of the X-ray and the Y-axis represents reflectivity.

Referring to FIG. 5, the second X-ray reflectivity spectrum is measured after the object (reference numerical 120 of FIG. 3) of silicon oxynitride is formed on the substrate. The measured second X-ray reflectivity spectrum is illustrated in FIG. 5. The object 120 has a deposited thickness of 400 Å.

Referring to FIG. 6, the graph is obtained by subtracting the first X-ray reflectivity spectrum of FIG. 4 from the second X-ray reflectivity spectrum of FIG. 5. In other words, FIG. 6 may be a graph corresponding to a difference between the first X-ray reflectivity spectrum of the substrate having the multi-layer and the second X-ray reflectivity spectrum of the substrate on which the object is formed. Thus, the variation of the X-ray reflectivity spectrum of just the object may be obtained.

Portion A in FIG. 6 is transformed using the fast-Fourier-transform. The fast-Fourier transformed portion A is illustrated in the graph of FIG. 7. In FIG. 7, the X-axis represents the thickness of the object and the Y-axis represents intensity. As illustrated in FIG. 7, a peak occurs at about 400 Å in the fast-Fourier transformed graph. In other words, the thickness of the formed object of about 400 Å can be relatively accurately measured. As a result, the thickness of the object may be easily measured by a simple transform, excluding influences of the structure, physical properties, and/or simulation of the object and without performance of any additional verifying processes.

In accordance with one or more of the aforementioned embodiments, a method for measuring the thickness of the object is provided in which X-ray reflectivities of the substrate before and after formation of the object are measured. Then, the variation between the X-ray reflectivities is transformed using the fast-Fourier-transform. Thus, influences from the structure, physical properties, and/or simulation of the object may be excluded. As a result, the thickness of the object can be more accurately measured without performance of any additional verifying processes.

In accordance with one embodiment, the object being measured may be one or more layers or elements for formation of a semiconductor device. In other embodiments, the object may be an object different from a semiconductor device including, but not limited to, formations that have one or more thin layers or objects in other areas of technology or manufacture. Also, while X-rays are used in the foregoing embodiments, light in a different spectrum may be used in other embodiments.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A method for analyzing an object, the method comprising:
    measuring a first X-ray reflectivity from a substrate before formation of the object, measuring the first X-ray reflectivity including measuring a first X-ray reflectivity spectrum;
    forming the object on the substrate;
    measuring a second X-ray reflectivity from the substrate after the formation of the object, measuring the second X-ray reflectivity includes measuring a second X-ray reflectivity spectrum;
    generating a delta spectrum between the first and second X-ray reflectivity spectrums, the delta spectrum corresponding to a variation between the first and second X-ray reflectivities;
    transforming the variation using a fast-Fourier transform; and
    determining a thickness of the object based on the transformed variation.

2. The method as claimed in claim 1, further comprising:
    irradiating an X-ray for measuring each of the first and second X-ray reflectivities at an angle of about 5 degrees or less with respect to a surface of the substrate.

3. The method as claimed in claim 1, wherein generating the delta spectrum includes subtracting a raw first X-ray reflectivity spectrum from a raw second X-ray reflectivity spectrum.

4. The method as claimed in claim 1, wherein the object is a layer or a pattern.

5. The method as claimed in claim 4, wherein the layer or pattern is included in a semiconductor device.

6. The method as claimed in claim 1, further comprising:
numerically expressing a full width at half maximum (FWMH) of a peak of a result obtained by fast-Fourier transforming the variation.

7. A method for analyzing an object, the method comprising:
measuring a first X-ray reflectivity from a substrate before formation of the object;
forming the object on the substrate;
measuring a second X-ray reflectivity from the substrate after the formation of the object;
calculating a variation between the first and second X-ray reflectivities;
transforming the calculated variation using a fast-Fourier transform;
numerically expressing a signal to noise ratio (S/N ratio) of a result obtained by fast-Fourier transforming the calculated variation; and
determining a thickness of the object based on the S/N ratio of the result obtained by fast-Fourier transforming the calculated variation.

8. A method for analyzing an object, the method comprising:
measuring a first reflectivity of light from a surface;
measuring a second reflectivity of light from the object, after the object is formed on the surface;
calculating a variation between the first and second reflectivities;
transforming the variation using a predetermined transform; and
determining a thickness of the object based on the transformed variation, wherein the method further includes numerically expressing a full width at half maximum (FWMH) of a peak of a result obtained by the predetermined transform.

9. The method as claimed in claim 8, wherein the light is in an X-ray spectrum.

10. The method as claimed in claim 8, wherein the predetermined transform is a fast-Fourier transform.

11. The method as claimed in claim 8, further comprising:
irradiating light on the surface at a first angle; and
irradiating light on the object at a second angle.

12. The method as claimed in claim 11, wherein the first angle is substantially equal to the second angle.

13. The method as claimed in claim 11, wherein the first and second angles are in a range of about 5 degrees or less.

14. The method as claimed in claim 8, wherein:
measuring the first reflectivity includes measuring a first reflectivity spectrum; and
measuring the second reflectivity includes measuring a second reflectivity spectrum.

15. The method as claimed in claim 14, wherein calculating the variation includes subtracting a raw first reflectivity spectrum from a raw second reflectivity spectrum.

16. The method as claimed in claim 8, wherein:
the surface is a surface of a semiconductor substrate; and
the object is a formation on the surface of the semiconductor substrate.

17. The method as claimed in claim 8, further comprising:
numerically expressing a signal to noise ratio (S/N ratio) of a result obtained by the predetermined transform.

* * * * *